(12) United States Patent
Sowards et al.

(10) Patent No.: US 12,376,794 B2
(45) Date of Patent: Aug. 5, 2025

(54) OPTICAL AND ELECTRICAL DIAGNOSTIC SYSTEMS AND METHODS THEREOF

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 18/607,165

(22) Filed: Mar. 15, 2024

(65) Prior Publication Data

US 2024/0215917 A1 Jul. 4, 2024

Related U.S. Application Data

(62) Division of application No. 17/217,852, filed on Mar. 30, 2021, now Pat. No. 11,931,179.

(Continued)

(51) Int. Cl.
*A61B 5/107* (2006.01)
*A61B 5/00* (2006.01)
(Continued)

(52) U.S. Cl.
CPC .......... *A61B 5/6852* (2013.01); *A61B 5/1076* (2013.01); *A61M 25/0067* (2013.01); *A61B 2034/2061* (2016.02)

(58) Field of Classification Search
CPC ....................... A61B 2034/2061; A61B 5/1076
See application file for complete search history.

(56) References Cited

U.S. PATENT DOCUMENTS 3,493,288 A  2/1970 Oltman et al.
4,768,855 A  9/1988 Nishi et al.
(Continued)

FOREIGN PATENT DOCUMENTS

CA      3025240 A1    11/2017
DE  102016109601 A1    11/2017
(Continued)

OTHER PUBLICATIONS

PCT/US2023/015536 filed Mar. 17, 2023 International Preliminary Report on Patentability dated Sep. 10, 2024.
(Continued)

*Primary Examiner* — Daniel L Cerioni
(74) *Attorney, Agent, or Firm* — Rutan & Tucker LLP

(57) ABSTRACT

Optical-and-electrical medical systems and methods thereof are disclosed. Such a medical system can include a console, an optical shape-sensing ("OSS") medical device including an optical-fiber stylet, one or more electrical medical devices, and a relay module for establishing one or more optical or electrical relay connections between the relay module and a remainder of the medical system including the console. The console can be configured for converting reflected optical signals from the optical-fiber stylet into shapes thereof for display. The relay module can include a primary receptacle configured to accept insertion of a medical barrier-piercing plug of the OSS medical device and establish a through-barrier optical connection therebetween. The relay module also can include one or more secondary receptacles configured to accept insertion of a corresponding number of electrical plugs of the one-or-more electrical medical devices and establish one or more under-barrier electrical connections therebetween.

11 Claims, 6 Drawing Sheets

Related U.S. Application Data

(60) Provisional application No. 63/002,041, filed on Mar. 30, 2020.

(51) Int. Cl.
*A61M 25/00* (2006.01)
*A61B 34/20* (2016.01)

(56) References Cited

U.S. PATENT DOCUMENTS

| | | |
|---|---|---|
| 4,813,429 A | 3/1989 | Eshel et al. |
| 5,099,845 A | 3/1992 | Besz et al. |
| 5,163,935 A | 11/1992 | Black et al. |
| 5,178,153 A | 1/1993 | Einzig |
| 5,207,672 A | 5/1993 | Roth et al. |
| 5,211,165 A | 5/1993 | Dumoulin et al. |
| 5,220,703 A | 6/1993 | Kanayama et al. |
| 5,275,151 A | 1/1994 | Shockey et al. |
| 5,295,212 A | 3/1994 | Morton et al. |
| 5,423,321 A | 6/1995 | Fontenot |
| 5,454,807 A | 10/1995 | Lennox et al. |
| 5,517,997 A | 5/1996 | Fontenot |
| 5,599,492 A | 2/1997 | Engelson |
| 5,622,170 A | 4/1997 | Schulz |
| 5,633,494 A | 5/1997 | Danisch |
| 5,693,043 A | 12/1997 | Kittrell et al. |
| 5,740,808 A | 4/1998 | Panescu et al. |
| 5,827,313 A | 10/1998 | Ream |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 5,957,831 A | 9/1999 | Adair |
| 6,035,229 A | 3/2000 | Silverstein et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,210,362 B1 | 4/2001 | Ponzi |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,563,105 B2 | 5/2003 | Seibel et al. |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,619,857 B2 | 9/2003 | Miyake |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 6,975,803 B2 | 12/2005 | Koide et al. |
| 7,043,287 B1 | 5/2006 | Khalil et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,699,855 B2 | 4/2010 | Anderson et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,182,433 B2 | 5/2012 | Leo et al. |
| 8,187,189 B2 | 5/2012 | Jung et al. |
| 8,197,494 B2 | 6/2012 | Jaggi et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,622,935 B1 | 1/2014 | Leo |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,119,551 B2 | 9/2015 | Qi et al. |
| 9,186,046 B2 | 11/2015 | Ramamurthy et al. |
| 9,339,206 B2 | 5/2016 | Grunwald |
| 9,339,221 B1 | 5/2016 | Heaton, II et al. |
| 9,345,510 B2 | 5/2016 | Patel et al. |
| 9,360,630 B2 | 6/2016 | Jenner et al. |
| 9,549,685 B2 | 1/2017 | Cox et al. |
| 9,560,954 B2 | 2/2017 | Jacobs et al. |
| 9,572,492 B2 | 2/2017 | Simpson et al. |
| 9,622,706 B2 | 4/2017 | Dick et al. |
| 9,645,326 B1 | 5/2017 | Sausse et al. |
| 9,649,048 B2 | 5/2017 | Cox et al. |
| 9,678,275 B1 | 6/2017 | Griffin |
| 9,678,284 B2 | 6/2017 | Coggi et al. |
| 9,737,213 B1 | 8/2017 | Heaton, II et al. |
| 9,872,978 B1 | 1/2018 | Zaborsky et al. |
| 10,231,643 B2 | 3/2019 | Grunwald |
| 10,231,753 B2 | 3/2019 | Burnside et al. |
| 10,258,240 B1 | 4/2019 | Eberle et al. |
| 10,265,133 B1 | 4/2019 | McClellan |
| 10,327,830 B2 | 6/2019 | Grant et al. |
| 10,349,890 B2 | 7/2019 | Misener et al. |
| 10,448,837 B2 | 10/2019 | Manzke et al. |
| 10,492,876 B2 | 12/2019 | Anastassiou et al. |
| 10,551,245 B2 | 2/2020 | Do et al. |
| 10,568,586 B2 | 2/2020 | Begin et al. |
| 10,603,126 B2 | 3/2020 | Karguth et al. |
| 10,620,386 B2 | 4/2020 | Van Der Mark et al. |
| 10,631,718 B2 | 4/2020 | Petroff et al. |
| 10,932,670 B2 | 3/2021 | Smith et al. |
| 10,939,889 B2 | 3/2021 | Flexman et al. |
| 10,992,078 B2 | 4/2021 | Thompson et al. |
| 10,992,079 B2 | 4/2021 | Stats et al. |
| 11,000,207 B2 | 5/2021 | Burnside et al. |
| 11,000,265 B1 | 5/2021 | Ryu et al. |
| 11,103,321 B2 | 8/2021 | Braun et al. |
| 11,123,047 B2 | 9/2021 | Jaffer et al. |
| 11,259,892 B2 | 3/2022 | Hufford et al. |
| 11,284,916 B2 | 3/2022 | Patel et al. |
| 11,369,342 B2 | 6/2022 | Irisawa |
| 11,382,653 B2 | 7/2022 | Patel et al. |
| 11,474,310 B2 | 10/2022 | Sowards et al. |
| 11,525,670 B2 | 12/2022 | Messerly et al. |
| 11,547,282 B2 | 1/2023 | Weise et al. |
| 11,607,150 B2 | 3/2023 | Schweikert et al. |
| 11,621,518 B2 | 4/2023 | Stats et al. |
| 11,630,009 B2 | 4/2023 | Misener et al. |
| 11,707,205 B2 | 7/2023 | Messerly et al. |
| 11,806,096 B2 | 11/2023 | Flatt et al. |
| 11,850,073 B2 | 12/2023 | Wright et al. |
| 11,931,112 B2 | 3/2024 | Thompson et al. |
| 12,038,338 B2 | 7/2024 | Misener et al. |
| 12,048,478 B2 | 7/2024 | Tegg et al. |
| 12,089,815 B2 | 9/2024 | Sowards et al. |
| 2002/0019627 A1 | 2/2002 | Maguire et al. |
| 2002/0087206 A1 | 7/2002 | Hirschberg et al. |
| 2002/0166190 A1 | 11/2002 | Miyake et al. |
| 2002/0188285 A1 | 12/2002 | Brown |
| 2002/0198457 A1 | 12/2002 | Tearney et al. |

(56) References Cited

U.S. PATENT DOCUMENTS

| | | |
|---|---|---|
| 2003/0045798 A1 | 3/2003 | Hular et al. |
| 2003/0092995 A1 | 5/2003 | Thompson |
| 2004/0039274 A1 | 2/2004 | Benaron et al. |
| 2004/0111020 A1 | 6/2004 | Long |
| 2004/0111147 A1 | 6/2004 | Rabkin et al. |
| 2004/0242995 A1 | 12/2004 | Maschke |
| 2004/0247268 A1 | 12/2004 | Ishihara et al. |
| 2004/0260182 A1 | 12/2004 | Zuluaga et al. |
| 2005/0033264 A1 | 2/2005 | Redinger |
| 2005/0113719 A1 | 5/2005 | Saadat |
| 2005/0272975 A1 | 12/2005 | McWeeney et al. |
| 2006/0013523 A1 | 1/2006 | Childlers et al. |
| 2006/0030753 A1 | 2/2006 | Boutillette et al. |
| 2006/0036164 A1 | 2/2006 | Wilson et al. |
| 2006/0069305 A1 | 3/2006 | Couvillon et al. |
| 2006/0100610 A1 | 5/2006 | Wallace et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Larkin et al. |
| 2007/0179485 A1 | 8/2007 | Yeik et al. |
| 2007/0201793 A1 | 8/2007 | Askins et al. |
| 2007/0225563 A1 | 9/2007 | Ogino |
| 2007/0253673 A1 | 11/2007 | Nielsen et al. |
| 2007/0265503 A1 | 11/2007 | Schlesinger et al. |
| 2007/0287886 A1 | 12/2007 | Saadat |
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 | 1/2009 | Dick et al. |
| 2009/0046980 A1 | 2/2009 | Rohlen |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0304582 A1 | 12/2009 | Rousso et al. |
| 2009/0318757 A1 | 12/2009 | Singh |
| 2009/0324161 A1 | 12/2009 | Prisco |
| 2010/0016729 A1 | 1/2010 | Futrell |
| 2010/0030063 A1 | 2/2010 | Lee et al. |
| 2010/0063534 A1 | 3/2010 | Kugler et al. |
| 2010/0114115 A1 | 5/2010 | Schlesinger et al. |
| 2010/0114190 A1 | 5/2010 | Bendett et al. |
| 2010/0139669 A1 | 6/2010 | Piferi et al. |
| 2010/0204569 A1 | 8/2010 | Burnside et al. |
| 2010/0286531 A1 | 11/2010 | Ryan et al. |
| 2010/0292758 A1 | 11/2010 | Lee et al. |
| 2011/0087112 A1 | 4/2011 | Leo et al. |
| 2011/0098533 A1 | 4/2011 | Onoda et al. |
| 2011/0144481 A1 | 6/2011 | Feer et al. |
| 2011/0144630 A1 | 6/2011 | Loeb |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0116161 A1 | 5/2012 | Nieman et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0031674 A1 | 1/2014 | Newman et al. |
| 2014/0046261 A1 | 2/2014 | Newman et al. |
| 2014/0058368 A1 | 2/2014 | Hogue |
| 2014/0073950 A1 | 3/2014 | Akui et al. |
| 2014/0088413 A1 | 3/2014 | Von Bucsh et al. |
| 2014/0121468 A1 | 5/2014 | Eichenholz |
| 2014/0155948 A1 | 6/2014 | Walsh et al. |
| 2014/0180087 A1 | 6/2014 | Millett et al. |
| 2014/0188133 A1 | 7/2014 | Misener |
| 2014/0221829 A1 | 8/2014 | Maitland et al. |
| 2014/0259477 A1 | 9/2014 | Huang |
| 2014/0268167 A1 | 9/2014 | Friedman et al. |
| 2014/0275997 A1 | 9/2014 | Chopra et al. |
| 2014/0318825 A1 | 10/2014 | Erb et al. |
| 2014/0323887 A1 | 10/2014 | Anderson et al. |
| 2014/0378945 A1 | 12/2014 | Beri |
| 2015/0029511 A1 | 1/2015 | 'T Hooft et al. |
| 2015/0031987 A1 | 1/2015 | Pameijer et al. |
| 2015/0045649 A1 | 2/2015 | O'Dea et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0272445 A1 | 10/2015 | Rozental et al. |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0290542 A1 | 10/2017 | Chandrasoma |
| 2017/0296037 A1 | 10/2017 | Yoshino |
| 2017/0303824 A1 | 10/2017 | Schlesinger et al. |
| 2017/0311924 A1 | 11/2017 | Sudol |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0093078 A1 | 4/2018 | Patil et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |

(56) References Cited

U.S. PATENT DOCUMENTS

| | | |
|---|---|---|
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0317751 A1 | 11/2018 | Kuboi et al. |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0192818 A1 | 6/2019 | Koda et al. |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0022587 A1 | 1/2020 | Glover et al. |
| 2020/0046434 A1 | 2/2020 | Graetzel et al. |
| 2020/0060718 A1 | 2/2020 | Patel et al. |
| 2020/0069192 A1 | 3/2020 | Sanborn et al. |
| 2020/0093353 A1 | 3/2020 | Tezuka et al. |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0238051 A1 | 7/2020 | Hwang et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0290315 A1 | 9/2021 | Lampert et al. |
| 2021/0298680 A1 | 9/2021 | Sowards et al. |
| 2021/0299879 A1 | 9/2021 | Pinter et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0039632 A1 | 2/2022 | Polejaev et al. |
| 2022/0039744 A1 | 2/2022 | Koenig |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2022/0361762 A1 | 11/2022 | Lalancette et al. |
| 2023/0082991 A1 | 3/2023 | Sowards et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0423456 A1 | 12/2024 | Sowards et al. |
| 2025/0176853 A1 | 6/2025 | Sowards et al. |
| 2025/0186134 A1 | 6/2025 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 3545849 A1 | 10/2019 |
| EP | 3725252 A1 | 10/2020 |
| WO | 9964099 A1 | 12/1999 |
| WO | 2006080076 A1 | 8/2006 |
| WO | 2006122001 A2 | 11/2006 |
| WO | 2009155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016061431 A1 | 4/2016 |
| WO | 2016193051 A1 | 12/2016 |
| WO | 2018071490 A1 | 4/2018 |
| WO | 2018096491 A1 | 5/2018 |
| WO | 2019037071 A1 | 2/2019 |
| WO | 2019046769 A1 | 3/2019 |
| WO | 2019230713 A1 | 12/2019 |
| WO | 2020142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022031613 A1 | 2/2022 |
| WO | 2022081586 A1 | 4/2022 |
| WO | 2022081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

U.S. Appl. No. 17/191,551, filed Mar. 3, 2021 Non-Final Office Action dated Aug. 16, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Final Office Action dated Aug. 8, 2024.
U.S. Appl. No. 18/141,289, filed Apr. 28, 2023 Non-Final Office Action dated Sep. 28, 2024.

(56) References Cited

OTHER PUBLICATIONS

U.S. Appl. No. 18/524,620, filed Nov. 30, 2023 Notice of Allowance dated Sep. 12, 2024.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/187,536, filed Feb. 26, 2021 Final Office Action dated Jul. 2, 2024.
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.
U.S. Appl. No. 17/725,394, filed Apr. 20, 2022 Non-Final Office Action dated Jun. 17, 2024.
U.S. Appl. No. 17/849,447, filed Jun. 24, 2022 Non-Final Office Action dated Apr. 10, 2024.
U.S. Appl. No. 18/524,620, filed Nov. 30, 2023 Non-Final Office Action dated Jun. 18, 2024.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
PCT/US2021/059755 filed Nov. 17, 2021 International Search Report and Written Opinion dated Apr. 29, 2022.
PCT/US2021/060849 filed Nov. 24, 2021 International Search Report and Written Opinion dated Mar. 9, 2022.
PCT/US2022/024934 filed Apr. 14, 2022 International Search Report and Written Opinion dated Jul. 18, 2022.
PCT/US2022/043698 filed Sep. 15, 2022 International Search Report and Written Opinion dated Dec. 19, 2022.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020042 filed Apr. 26, 2023 International Search Report and Written Opinion dated Sep. 26, 2023.
PCT/US2023/020044 filed Apr. 26, 2023 International Search Report and Written Opinion dated Jul. 19, 2023.
PCT/US2023/025757 filed Jun. 20, 2023 International Search Report and Written Opinion dated Sep. 11, 2023.
PCT/US2023/027527 filed Jul. 12, 2023 International Search Report and Written Opinion dated Oct. 16, 2023.
U.S. Appl. No. 17/185,777, filed Feb. 25, 2021 Non-Final Office Action dated Feb. 9, 2022.
U.S. Appl. No. 17/185,777, filed Feb. 25, 2021 Notice of Allowance dated Jun. 10, 2022.
U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/187,536, filed Feb. 26, 2021 Non-Final Office Action dated Dec. 15, 2023.
U.S. Appl. No. 17/187,536, filed Feb. 26, 2021 Non-Final Office Action dated May 17, 2023.
U.S. Appl. No. 17/217,852, filed Mar. 30, 2021 Ex Parte Quayle Action dated Sep. 8, 2023.
U.S. Appl. No. 17/217,852, filed Mar. 30, 2021 Non Final Office Action dated Jun. 7, 2023.
U.S. Appl. No. 17/217,852, filed Mar. 30, 2021 Notice of Allowance dated Nov. 7, 2023.
U.S. Appl. No. 17/217,852, filed Mar. 30, 2021 Restriction Requirement dated Mar. 21, 2023.
U.S. Appl. No. 17/499,644, filed Oct. 12, 2021 Notice of Allowance dated Sep. 18, 2023.
U.S. Appl. No. 17/499,644, filed Oct. 12, 2021 Restriction Requirement dated Jul. 11, 2023.
U.S. Appl. No. 17/535,406, filed Nov. 24, 2021 Non-Final Office Action dated Feb. 15, 2024.
U.S. Appl. No. 17/535,406, filed Nov. 24, 2021 Restriction Requirement dated Nov. 24, 2023.
U.S. Appl. No. 17/689,773, filed Mar. 8, 2022 Non-Final Office Action dated Mar. 19, 2024.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
U.S. Appl. No. 17/697,895, filed Mar. 17, 2022 Non Final Office Action dated Jun. 14, 2023.
U.S. Appl. No. 17/697,895, filed Mar. 17, 2022 Non-Final Office Action dated Jan. 11, 2024.
U.S. Appl. No. 17/731,155, filed Apr. 27, 2022 Restriction Requirement dated Feb. 28, 2024.
U.S. Appl. No. 17/967,794, filed Oct. 17, 2022 Notice of Allowance dated Feb. 15, 2023.
PCT/US2023/018076 filed Apr. 10, 2023 International Preliminary Report on Patentability dated Oct. 8, 2024.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Notice of Allowance dated Nov. 8, 2024.
U.S. Appl. No. 17/529,022, filed Nov. 17, 2021 Notice of Allowance dated Jan. 2, 2025.
U.S. Appl. No. 17/529,022, filed Nov. 17, 2021 Restriction Requirement dated May 2, 2024.
U.S. Appl. No. 17/535,406, filed Nov. 24, 2021 Notice of Allowance dated Oct. 23, 2024.
U.S. Appl. No. 17/689,773, filed Mar. 8, 2022 Advisory Action dated Nov. 1, 2024.
U.S. Appl. No. 17/689,773, filed Mar. 8, 2022 Notice of Allowance dated Jan. 15, 2025.
U.S. Appl. No. 17/696,675, filed Mar. 16, 2022 Advisory Action dated Feb. 6, 2025.
U.S. Appl. No. 17/696,675, filed Mar. 16, 2022 Final Office Action dated Dec. 5, 2024.
U.S. Appl. No. 17/725,394, filed Apr. 20, 2022 Non-Final Office Action dated Nov. 19, 2024.
U.S. Appl. No. 17/731,129, filed Apr. 27, 2022 Restriction Requirement dated Feb. 28, 2025.
U.S. Appl. No. 17/731,155, filed Apr. 27, 2022 Final Office Action dated Jan. 24, 2025.
U.S. Appl. No. 17/849,447, filed Jun. 24, 2022 Advisory Action dated Oct. 24, 2024.
U.S. Appl. No. 17/849,447, filed Jun. 24, 2022 Non-Final Office Action dated Jan. 17, 2025.
U.S. Appl. No. 17/849,447, filed Jun. 24, 2022 Restriction Requirement dated Apr. 15, 2024.
U.S. Appl. No. 17/863,211, filed Jul. 12, 2022 Non-Final Office Action dated Jan. 29, 2025.

(56) References Cited

OTHER PUBLICATIONS

U.S. Appl. No. 17/863,211, filed Jul. 12, 2022 Restriction Requirement dated Nov. 15, 2024.
U.S. Appl. No. 17/945,875, filed Sep. 15, 2022 Non-Final Office Action dated Feb. 27, 2025.
U.S. Appl. No. 18/141,289, filed Apr. 28, 2023 Notice of Allowance dated Jan. 10, 2025.
U.S. Appl. No. 17/717,919, filed Apr. 11, 2022 Restriction Requirement dated Apr. 23, 2025.
U.S. Appl. No. 17/721,333, filed Apr. 14, 2022 Restriction Requirement dated May 6, 2025.
U.S. Appl. No. 17/725,394, filed Apr. 20, 2022 Advisory Action dated Jun. 5, 2025.
U.S. Appl. No. 17/725,394, filed Apr. 20, 2022 Final Office Action dated Mar. 27, 2025.
U.S. Appl. No. 17/731,129, filed Apr. 27, 2022 Non-Final Office Action dated Apr. 28, 2025.
U.S. Appl. No. 17/731,155, filed Apr. 27, 2022 Advisory Action dated Apr. 3, 2025.
U.S. Appl. No. 17/849,447, filed Jun. 24, 2022 Final Office Action dated May 7, 2025.
U.S. Appl. No. 17/863,211, filed Jul. 12, 2022 Final Office Action dated Jun. 3, 2025.
U.S. Appl. No. 18/075,280, filed Dec. 5, 2022 Non-Final Office Action dated Jun. 11, 2025.
U.S. Appl. No. 18/075,280, filed Dec. 5, 2022 Restriction Requirement dated Mar. 28, 2025.

OPTICAL AND ELECTRICAL DIAGNOSTIC SYSTEMS AND METHODS THEREOF

This application is a division of U.S. patent application Ser. No. 17/217,852, filed Mar. 30, 2021, now U.S. Pat. No. 11,931,179, which claims the benefit of priority to U.S. Provisional Application No. 63/002,041, filed Mar. 30, 2020, each of which is incorporated by reference in its entirety into this application.

BACKGROUND

At times, a tip of a peripherally inserted central catheter ("PICC") or central venous catheter ("CVC") can move becoming displaced from an ideal position in a patient's superior vena cava ("SVC"). A clinician believing such a PICC or CVC has displaced typically checks for displacement by chest X-ray and replaces the PICC or CVC if necessary. Because X-rays expose patients to ionizing radiation, medical devices such as PICCs and CVCs are being developed with integrated optical-fiber stylets for clinicians to check easily and safely for displacement thereof. However, in order for the clinicians to check for displacement, the PICCs or CVCs, which are sterile as provided, need to be at least optically connected to non-sterile capital equipment without compromising sterile conditions. Therefore, there is a need for an optical medical system that allows for single-use medical devices such as the foregoing PICCs and CVCs to be at least optically connected to non-sterile capital equipment without compromising sterile conditions. Disclosed herein are optical and electrical medical systems, and methods thereof.

SUMMARY

Disclosed herein is a relay module including, in some embodiments, a housing, a primary receptacle disposed in the housing, one or more secondary receptacles disposed in the housing, and one or more cables extending from the housing. The primary receptacle is configured to accept insertion of a barrier-piercing plug associated with an optical shape-sensing ("OSS") medical device and establish a through-barrier connection between the relay module and the OSS medical device. The through-barrier connection is selected from a through-barrier optical connection and a through-barrier optical-and-electrical connection. The one-or-more secondary receptacles are configured to accept insertion of a corresponding number of electrical plugs associated with one or more electrical medical devices and establish a corresponding number of under-barrier electrical connections between the relay module and the one-or-more electrical medical devices. The one-or-more cables include a corresponding number of relay-module plugs for establishing one or more relay connections between the relay module and a remainder of a medical system configured to receive optical and electrical signals from the relay module. The one-or-more relay connections are selected from a relay optical connection, a relay optical-and-electrical connection, and a relay electrical connection, provided at least the relay optical connection or the relay optical-and-electrical connection is selected.

In some embodiments, the relay module further includes an optical fiber having one or more optical-fiber cores extending from the primary receptacle through a primary cable of the one-or-more cables to a corresponding primary plug of the number of relay-module plugs. The optical fiber is configured to convey input optical signals from an optical interrogator of the medical system to an optical-fiber stylet of the OSS medical device once the through-barrier connection is established. The optical fiber is also configured to convey reflected optical signals from the optical-fiber stylet to the optical interrogator when the through-barrier connection is established.

In some embodiments, the relay module further includes one or more electrical leads extending from a number of receptacles including the primary receptacle and the one-or-more secondary receptacles through any cable of the one-or-more cables to the corresponding relay-module plug thereof. The one-or-more electrical leads are configured to convey electrical signals from the relay module to the medical system.

In some embodiments, the relay module further includes one or more sensors selected from a gyroscope, an accelerometer, and a magnetometer disposed within the housing. The one-or-more sensors are configured to provide sensor data for determining a reference plane for shape sensing with the OSS medical device.

In some embodiments, the relay module of further includes a light-emitting diode ("LED") disposed in the housing proximate the primary receptacle. The LED is configured to illuminate upon establishing the relay optical-and-electrical connection or any relay electrical connection of the number of relay electrical connections for finding the primary receptacle when the relay module is under a medical barrier.

In some embodiments, the relay module is amenable to high-level disinfection or sterilization.

In some embodiments, the housing includes a patient-facing surface configured to be adhered to a patient, thereby enabling the relay module to be secured to the patient.

Disclosed herein is a medical system including, in some embodiments, a console, an OSS medical device configured for shape sensing, one or more electrical medical devices, and a relay module. The console includes memory and one or more processors for converting reflected optical signals from an optical-fiber stylet into shapes thereof for display. The console further includes an integrated optical interrogator for converting the reflected optical signals into the shapes of the optical-fiber stylet. Alternatively, the console is communicatively coupled to a stand-alone optical interrogator configured for converting the reflected optical signals into the shapes of the optical-fiber stylet. The OSS medical device includes the optical-fiber stylet and a barrier-piercing plug. Each electrical medical device of the one-or-more electrical medical devices includes at least one electrical plug. The relay module includes a housing, a primary receptacle disposed in the housing, one or more secondary receptacles disposed in the housing, and one or more cables extending from the housing. The primary receptacle is configured to accept insertion of the barrier-piercing plug associated with the OSS medical device and establish a through-barrier connection between the relay module and the OSS medical device. The through-barrier connection is selected from a through-barrier optical connection and a through-barrier optical-and-electrical connection. The one-or-more secondary receptacles are configured to accept insertion of the at least one electrical plug of each electrical medical device of the one-or-more electrical medical devices and establish a corresponding number of under-barrier electrical connections between the relay module and the one-or-more electrical medical devices. The one-or-more cables include a corresponding number of relay-module plugs for establishing one or more relay connections between the relay module and either the console or a combination of the console and the stand-alone optical interrogator. The one-or-more relay connections are selected from a relay optical connection, a relay optical-and-electrical connection, and a relay electrical connection, provided at least the relay optical connection or the relay optical-and-electrical connection is selected.

In some embodiments, the relay module further includes an optical fiber having one or more optical-fiber cores extending from the primary receptacle through a primary cable of the one-or-more cables to a corresponding primary plug of the number of relay-module plugs. The optical fiber is configured to convey input optical signals from either the integrated optical interrogator or the stand-alone optical interrogator to the optical-fiber stylet of the OSS medical device once the through-barrier connection is established. The optical fiber is also configured to convey reflected optical signals from the optical-fiber stylet to the integrated optical interrogator or the stand-alone optical interrogator when the through-barrier connection is established.

In some embodiments, the relay module further includes one or more electrical leads extending from a number of receptacles including the primary receptacle and the one-or-more secondary receptacles through any cable of the one-or-more cables to the corresponding relay-module plug thereof. The one-or-more electrical leads are configured to convey electrical signals from the relay module to the console.

In some embodiments, the relay module further includes one or more relay module-based sensors selected from a gyroscope, an accelerometer, and a magnetometer disposed within the housing. The one-or-more relay module-based sensors are configured to provide relay module-based sensor data for determining a reference plane for shape sensing with the OSS medical device.

In some embodiments, the relay module of further includes an LED disposed in the housing proximate the primary receptacle. The LED is configured to illuminate upon establishing an electrical connection of the one-or-more relay connections for finding the primary receptacle when the relay module is under a medical barrier.

In some embodiments, the relay module is amenable to high-level disinfection or sterilization.

In some embodiments, the housing includes a patient-facing surface configured to be adhered to a patient, thereby enabling the relay module to be secured to the patient.

In some embodiments, the one-or-more electrical medical devices include one or more electrocardiogram ("ECG") patches.

In some embodiments, the one-or-more electrical medical devices include an arm band. The arm band has one or more arm band-based sensors selected from an arm band-based gyroscope, accelerometer, and magnetometer. The one-or-more arm band-based sensors are configured to provide arm band-based sensor data for reference-plane determination for the shape sensing with the OSS medical device.

Also disclosed herein is a method of a medical system. The method includes, in some embodiments, a relay-module placing step, an electrical-plug inserting step, a medical-drape placing step, and a barrier-piercing-plug inserting step. The relay-module placing step includes placing a relay module on a surface. The electrical-plug inserting step includes inserting one or more electrical plugs corresponding to one or more electrical medical devices into a corresponding number of secondary receptacles of the relay module. The electrical-plug inserting step establishes one or more under-barrier electrical connections between the one-or-more electrical devices and the relay module. The medi-cal-drape placing step includes placing a medical barrier over the relay module. The medical-drape placing step establishes a sterile field over the relay module. The barrier-piercing-plug inserting step includes inserting a barrier-piercing plug of an OSS medical device through the medical barrier and into a primary receptacle of the relay module. The barrier-piercing-plug inserting step establishes a through-barrier optical connection or a through-barrier optical-and-electrical connection between the OSS medical device in a sterile field and the relay module in a non-sterile field.

In some embodiments, the relay-module placing step includes placing the relay module on a chest of a patient. The relay-module placing step establishes a reference plane for shape sensing with the OSS medical device.

In some embodiments, the method further includes an identifying step and a palpating step. The identifying step includes identifying an illuminated LED disposed in a housing of the relay module proximate the primary receptacle. The palpating step includes palpating the primary receptacle under the medical barrier. Both the identifying step and the palpating step occur before the barrier-piercing-plug inserting step.

In some embodiments, the method further includes an establishing step of establishing one or more relay connections between the relay module and a remainder of the medical system for relaying optical and electrical signals from the relay module. The one-or-more relay connections are selected from a relay optical connection, a relay optical-and-electrical connection, and a relay electrical connection, provided at least the relay optical connection or the relay optical-and-electrical connection is selected.

These and other features of the concepts provided herein will become more apparent to those of skill in the art in view of the accompanying drawings and following description, which describe particular embodiments of such concepts in greater detail.

DESCRIPTION

Figure 1:
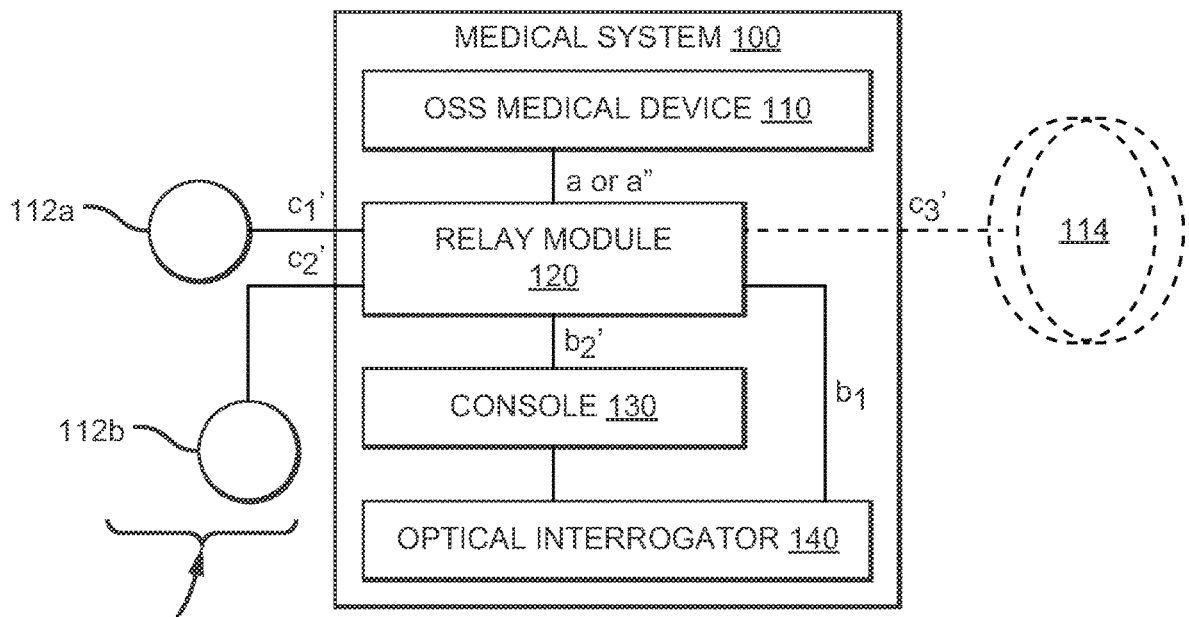
FIG. 1 is a block diagram of a first medical system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need for an optical medical system that allows for single-use medical devices such as the foregoing PICCs and CVCs to be at least optically connected to non-sterile capital equipment without compromising sterile conditions. Disclosed herein are optical and electrical medical systems and methods thereof.

Features of the optical and electrical medical systems ("medical systems") provided herein will become more apparent with reference to the accompanying drawings and the following description, which provide particular embodiments of the medical systems in greater detail. For context, the medical systems are described first followed by medical devices and relay modules of the medical systems, as well as methods of the foregoing.

Medical Systems

Figure 2:
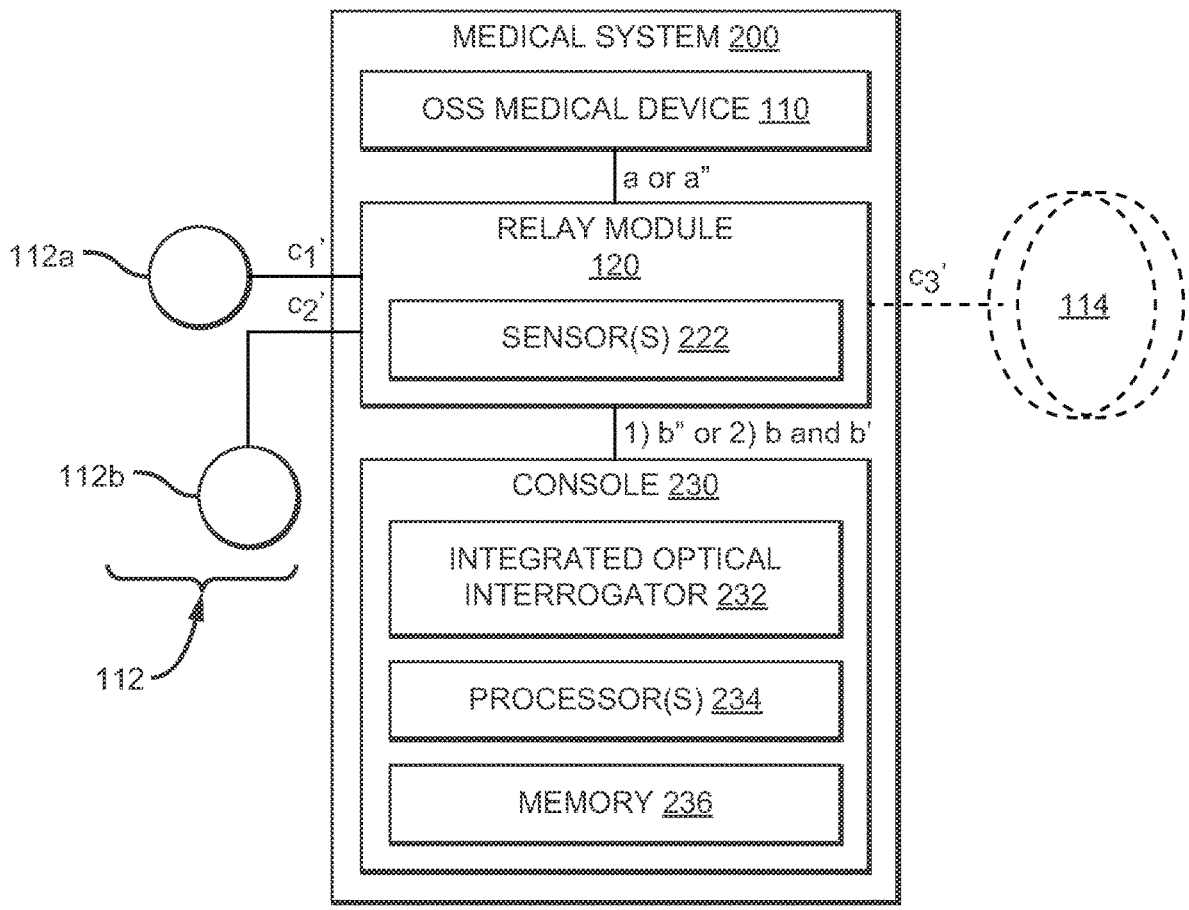
FIG. 2 is a block diagram of a second medical system in accordance with some embodiments.
Figure 3:
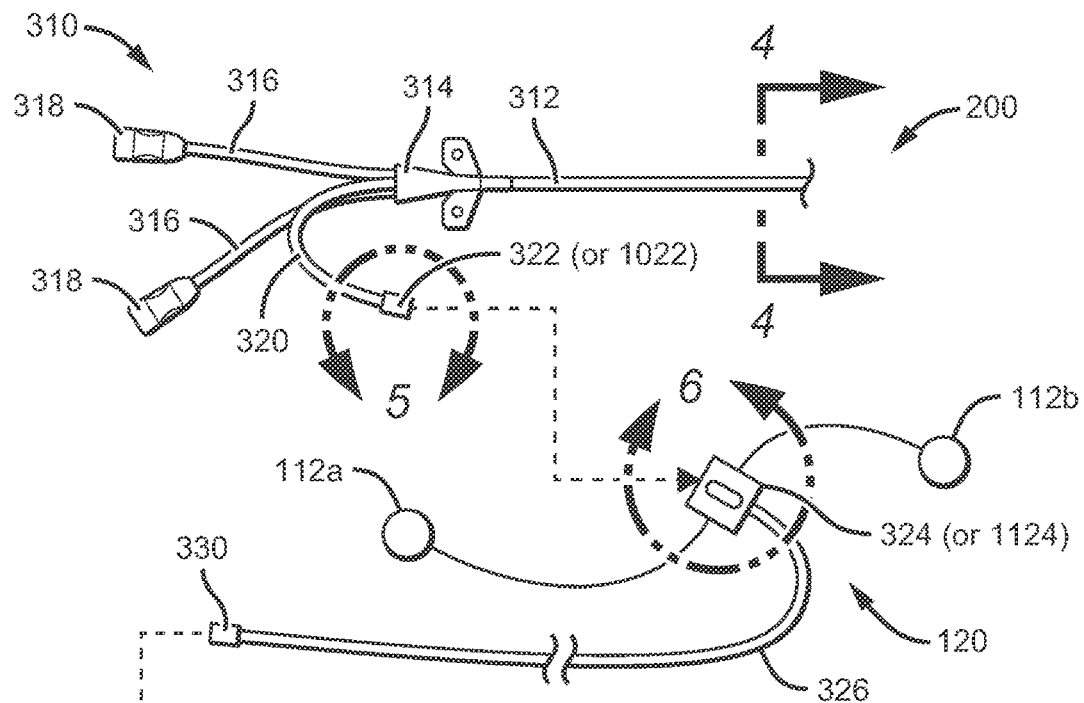
FIG. 3 illustrates the second medical system in accordance with some embodiments.
Figure 8:
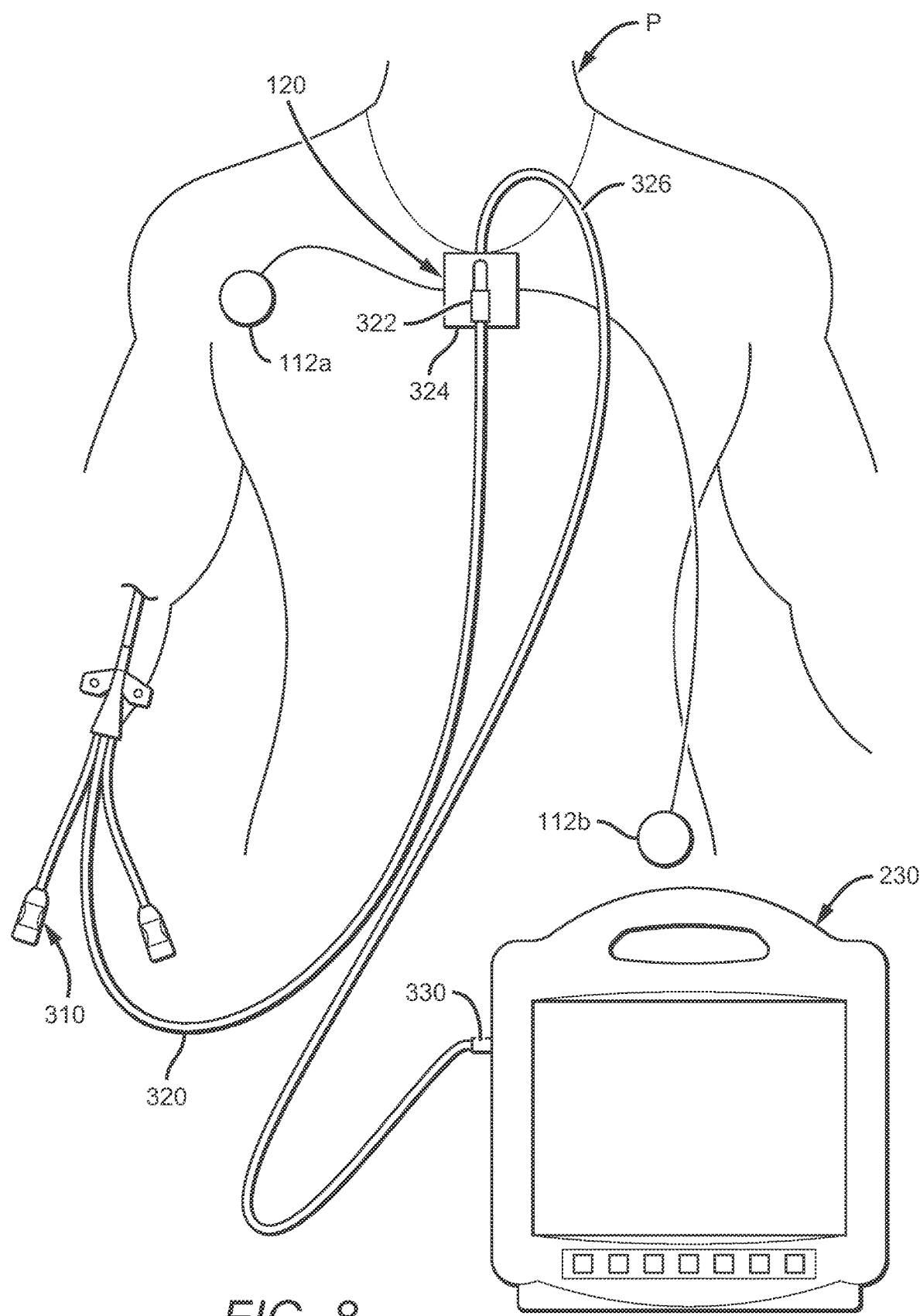
FIG. 8 illustrates the second medical system in use during a patient procedure in accordance with some embodiments.
Figure 9:
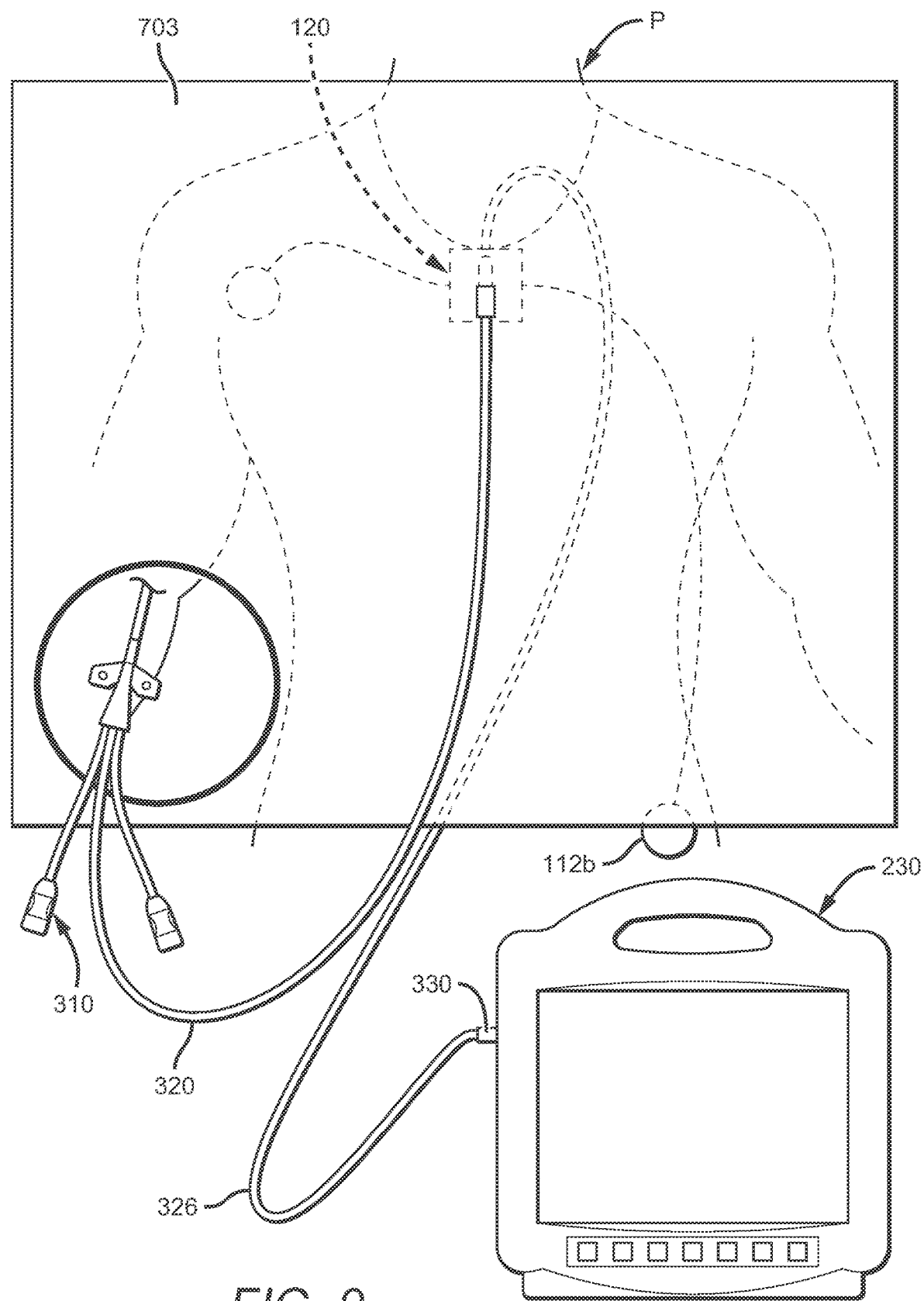
FIG. 9 illustrates the second medical system in use during a patient procedure with a medical barrier in accordance with some embodiments.

FIG. 1 is a block diagram of a first medical system 100 in accordance with some embodiments. FIG. 2 is a block diagram of a second medical system 200 in accordance with some embodiments. FIG. 3 illustrates the second medical system 200 in accordance with some embodiments. FIG. 8 illustrates the second medical system 200 in use during a patient procedure in accordance with some embodiments. FIG. 9 illustrates the second medical system 200 in use during a patient procedure with a medical barrier 703 in accordance with some embodiments.

As shown, the medical system 100 or 200 includes an OSS medical device 110, one or more electrical medical devices, a console 130 or 230, and a relay module 120 configured for connecting the OSS medical device 110 and the one-or-more electrical medical devices to a remainder of the medical system 100 or 200 such as the console 230. The OSS medical device 110 is typically used in a sterile field while the one-or-more electrical medical devices, the relay module 120, and the console 130 or 230 are typically used in a non-sterile field as defined by at least the medical barrier 703 (e.g., sterile drape).

The OSS medical device 110 includes at least an integrated optical-fiber stylet and a barrier-piercing plug. The optical-fiber stylet is a probe including one or more optical-fiber cores, wherein each core of the one-or-more optical-fiber cores has a number of fiber Bragg grating ("FBG") sensors along a length thereof for shape sensing with the medical system 100 or 200. (See integrated optical-fiber stylet 424 in FIG. 4 for an example of the optical-fiber stylet of the OSS medical device 110.) The barrier-piercing plug is configured to establish at least a through-barrier optical connection between the OSS medical device 110 and the relay module 120. (See barrier-piercing plug 322 in FIG. 3 for an example of the barrier-piercing plug of the OSS medical device 110.) However, the OSS medical device 110 can also include electrical componentry such as an electrocardiogram ("ECG") stylet and one or more electrical leads in support of the ECG stylet. As such, the barrier-piercing plug can be configured to establish a through-barrier optical-and-electrical connection between the OSS medical device 110 and the relay module 120 in some embodiments of the OSS medical device 110.

Certain features of the OSS medical device 110 are set forth in more detail below with respect to particular embodiments of the OSS medical device 110 such as the PICC 310. That said, some features (e.g., the optical fiber stylet, the ECG stylet, etc.) set forth below with respect to one or more embodiments of the OSS medical device 110 such as the PICC 310 can be shared among two or more embodiments of the OSS medical device 110. As such, "OSS medical device 110" is used herein to generically refer to more than one embodiment of the OSS medical device 110 when needed for expository expediency. This is despite certain features having been described with respect to particular embodiments of the OSS medical device 110 such as the PICC 310.

The one-or-more electrical medical devices can include, but are not limited to, electrocardiogram ("ECG") patches 112 (e.g., an ECG patch 112a configured as a right-arm ECG patch, an ECG patch 112b configured as a left-leg ECG patch, . . . , and an ECG patch 112n), a companion arm band 114, or both the ECG patches 112 and the arm band 114. Each electrical medical device of the one-or-more electrical medical devices includes at least one electrical plug configured to establish an electrical connection between the electrical device thereof and the relay module 120.

The arm band 114 can include one or more sensors selected from at least a gyroscope, an accelerometer, and a magnetometer disposed within the arm band 114. The one-or-more sensors are configured to provide sensor data to the console 130 or 230 by way of the relay module 120 for determining a reference plane for shape sensing with the optical-fiber stylet of the OSS medical device 110.

While only shown for the console 230, each console of the consoles 130 and 230 includes memory 236 and one or more processors 234 configured for at least converting reflected optical signals from the optical-fiber stylet of the OSS medical device 110 into displayable shapes for the OSS medical device 110. The displayable shapes for the OSS medical device 110 can be displayed on an integrated display screen integrated into the console 130 or 230 or a display screen of a stand-alone monitor coupled to the console 130 or 230. Each console of the consoles 130 and 230 can be further configured for converting electrical signals from the one-or-more electrical devices into displayable information for the one-or-more electrical devices. For example, for the optional ECG stylet or any ECG patch of the ECG patches 112, the console 130 or 230 can be configured to convert the electrical signals therefrom into an ECG trace for display. Such ECG traces can be useful in combination with the displayable shapes for the OSS medical device 110 for determining if the OSS medical device 110 has been displaced from its ideal position.

The medical system 100 further includes a stand-alone optical interrogator 140 communicatively coupled to the console 130, whereas the medical system 200 further includes an integrated optical interrogator 232 integrated into the console 230. The optical interrogator 140 or 232 is configured to send input optical signals into the optical-fiber stylet of the OSS medical device 110 by way of the relay module 120 and receive reflected optical signals from the optical-fiber stylet by way of the relay module 120. The optical interrogator 140 or 232 can be further configured to provide data to the console 130 or 230 corresponding to the reflected optical signals received for converting the reflected optical signals from the optical-fiber stylet of the OSS medical device 110 into the displayable shapes for the OSS medical device 110.

The relay module 120 includes a housing 324, a cable 326 extending from the housing 324, one or more optical-fiber cores 628 ("optical fiber 628") extending through the housing 324 and along the cable 326, and one or more electrical leads extending through the housing 324 and along the cable 326 or another cable. (See FIG. 6 for the optical fiber 628.)

The relay module 120 is configured to establish at least an optical connection (e.g., a through-barrier optical connection) between the optical-fiber stylet of the OSS medical device 110 and the optical fiber 628 of the relay module 120. (See connections a and a" in FIGS. 1 and 2, each connection of which includes at least an optical connection.) The relay module 120 is also configured with a plug 330 at a terminus of the cable 326 to establish at least another optical connection but between the optical fiber 628 of the relay module 120 and the stand-alone optical interrogator 140 or the console 230 including the integrated optical interrogator 232. (See connection $b_1$ in FIG. 1 and connection b or b" in FIG. 2, each connection of which includes at least an optical connection.) The optical fiber 628 of the relay module 120 is configured to convey the input optical signals from the optical interrogator 140 or 232 to the optical-fiber stylet of the OSS medical device 110 and the reflected optical signals from the optical-fiber stylet to the optical interrogator 140 or 232.

The relay module 120 can also be configured to establish an electrical connection (e.g., a through-barrier electrical connection) between any electrical componentry of the OSS medical device 110 and the one-or-more electrical leads of the relay module 120, which electrical connection can be simultaneously established with the optical connection in an electrical-and-optical connection. (See connections a" in FIGS. 1 and 2, each connection of which includes both an electrical-and-optical connection.) The plug 330 at the terminus of the cable 326 can be configured to establish another electrical connection but between the one-or-more electrical leads of the relay module 120 and the console 230 (i.e., the console 230 including the integrated optical interrogator 232). Such an electrical connection can be simultaneously established with the optical connection to the console 230 in another electrical-and-optical connection. (See connection b" in FIG. 2, which includes both an electrical-and-optical connection.) Alternatively, another plug at a terminus of another cable of the relay module 120 can be configured to establish the other electrical connection between the one-or-more electrical leads of the relay module 120 and the console 130 or 230. (See connection $b_2'$ in FIG. 1 and b' in FIG. 2, each connection of which includes at least an electrical connection.) The one-or-more electrical leads of the relay module 120 are configured to convey electrical signals from any electrical componentry of the OSS medical device 110 to the console 130 or 230.

Exclusive of the electrical connection between any electrical componentry of the OSS medical device 110 and the one-or-more electrical leads of the relay module 120, the relay module 120 can be configured to establish an electrical connection (e.g., an under-barrier electrical connection) between any electrical medical device of the one-or-more electrical medical devices (e.g., any ECG patch of the ECG patches 112, the arm band 114, etc.) and the one-or-more electrical leads of the relay module 120. (See connections $c_1'$, $c_2'$, and $c_3'$ in FIGS. 1 and 2, each connection of which includes at least an electrical connection.) As set forth above, the plug 330 at the terminus of the cable 326 can be configured to establish the other electrical connection between the one-or-more electrical leads of the relay module 120 and the console 230 (i.e., the console 230 including the integrated optical interrogator 232). Such an electrical connection can be simultaneously established with the optical connection to the console 230 in the other electrical-and-optical connection. (See connection b" in FIG. 2, which includes both an electrical-and-optical connection.) Alternatively, the other plug at the terminus of the other cable of the relay module 120 can be configured to establish the other electrical connection between the one-or-more electrical leads of the relay module 120 and the console 130 or 230. (See connection b' in FIG. 1 and b' in FIG. 2, each connection of which includes at least an electrical connection.) The one-or-more electrical leads of the relay module 120 are configured to convey electrical signals from the one-or-more electrical devices to the console 130 or 230.

It should be understood from the foregoing that a-type connections or through-barrier connections are between the OSS medical device 110 and the relay module 120, b-type connections or relay connections are between the relay module 120 and a remainder of the medical system 100 or 200 (e.g., a combination of the console 130 and the stand-alone optical interrogator 140 or the console 230 with the integrated optical interrogator 232), and c-type connections or under-barrier connections are between the one-or-more electrical medical devices and the relay module 120. A subscripted number associated with any type of connection of the a-, b-, and c-type connections numerically identifies a particular connection of a number of the a-, b-, or c-type connections. Lastly, an a-, b-, or c-type connection without a prime ("'") or double prime ("''") indicates an optical connection, an a-, b-, or c-type connection with a prime (e.g., "a'") indicates an electrical connection, and an a-, b-, or c-type connection with a double prime (e.g., "a''") indicates an optical-and-electrical connection.

The relay module 120 can further include one or more sensors 222 selected from at least a gyroscope, an accelerometer, and a magnetometer disposed within the housing 324. The one-or-more sensors 222 are configured to provide sensor data to the console 130 or 230 by way of the one-or-more electrical leads within the housing 324 and the cable 326 (or the other cable set forth above with respect to connection $b_2$' in FIG. 1 and b' in FIG. 2) for determining a reference plane for shape sensing with the optical-fiber stylet of the OSS medical device 110.

Certain features of the relay module 120 are set forth in more detail below with respect to particular embodiments of the relay module 120. That said, some features set forth below with respect to one or more embodiments of the relay module 120 are shared among two or more embodiments of the relay module 120 such as the relay module 1120. As such, "relay module 120" is used herein to generically refer to more than one embodiment of the relay module 120 when needed for expository expediency. This is despite certain features having been described with respect to particular embodiments of the relay module 120.

Medical Devices

Figure 4:
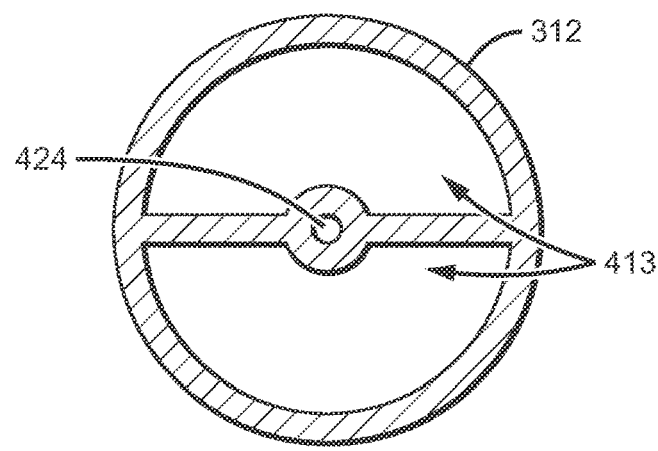
FIG. 4 illustrates a cross-section of a catheter tube of an OSS medical device in accordance with some embodiments.
Figure 5:
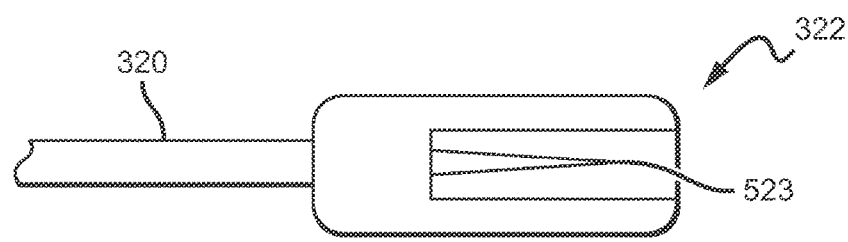
FIG. 5 illustrates a barrier-piercing plug of an extension tube of the OSS medical device for establishing an optical or optical-and-electrical connection in accordance with some embodiments.

FIG. 3 also illustrates a PICC 310 as the OSS medical device 110 in accordance with some embodiments. FIG. 4 illustrates a cross-section of a catheter tube 312 of the PICC 310 including an integrated optical-fiber stylet 424 in accordance with some embodiments. FIG. 5 illustrates a barrier-piercing plug 322 of an extension tube or cable 320 of the PICC 310 for establishing an optical or optical-and-electrical connection in accordance with some embodiments.

As shown, the PICC 310 includes the catheter tube 312, a bifurcated hub 314, two extension legs 316, and two Luer connectors 318 operably connected in the foregoing order. The catheter tube 312 includes two catheter-tube lumens 413 and the optical-fiber stylet 424 disposed in a longitudinal bead of the catheter tube 312 such as between the two catheter-tube lumens 413, as extruded. Optionally, in a same or different longitudinal bead of the catheter tube 312, the PICC 310 can further include the ECG stylet. The bifurcated hub 314 has two hub lumens correspondingly fluidly connected to the two catheter-tube lumens 413. Each extension leg of the two extension legs 316 has an extension-leg lumen fluidly connected to a hub lumen of the two hub lumens. The PICC 310 further includes the extension tube 320 either extending from the bifurcated hub 314 or communicatively coupled to the bifurcated hub 314. When extending from the bifurcated hub 314, the extension tube 320 can be a skived portion of the catheter tube 312 including the optical-fiber stylet 424 and, if present, the ECG stylet, which extension tube 320 can terminate in the plug 322 for establishing an optical connection between the optical-fiber stylet 424 of the PICC 310 and the optical fiber 628 of the relay module 120, as well as any electrical connections. The skived portion of the catheter tube 312 can be disposed in another tube, which, in combination, forms the extension tube 320 terminating in the plug 322 for establishing the foregoing optical and electrical connections.

While the PICC 310 is provided as a particular embodiment of the OSS medical device 110 of the medical system 100 or 200, it should be understood that any of a number of medical devices including catheters such as a CVC can include at least an optical-fiber stylet and, optionally, electrical componentry such as the ECG stylet and the one-or-more electrical leads in support thereof, terminating in a plug for establishing an optical or optical-and-electrical connection between the medical device and the relay module 120.

Relay Modules

Figure 6:
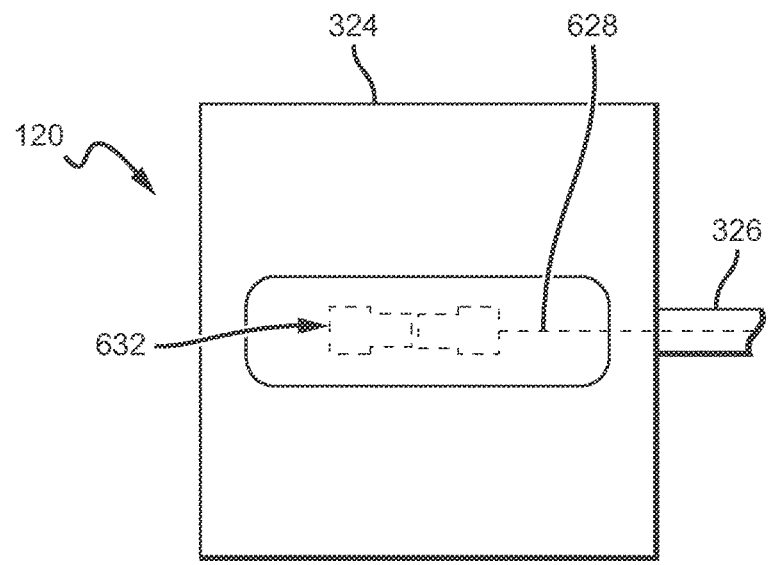
FIG. 6 illustrates a detailed view of a relay module with a primary receptacle for establishing optical or optical-and-electrical connections in accordance with some embodiments.
Figure 7:
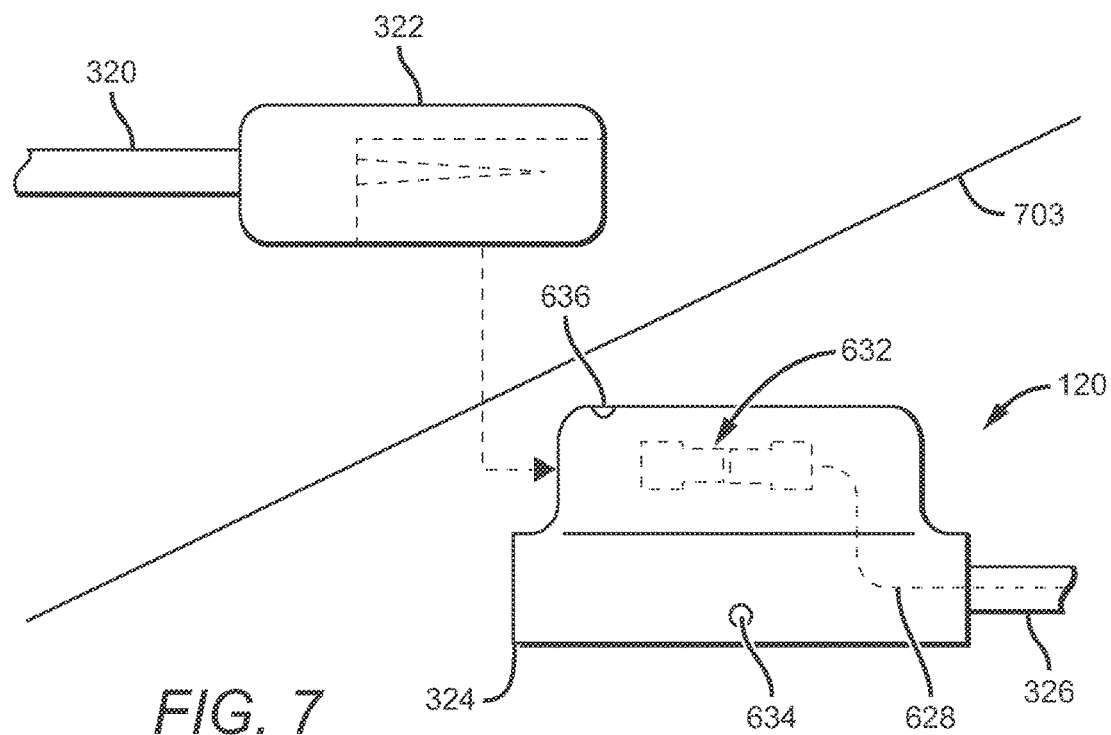
FIG. 7 illustrates establishing a through-barrier optical connection or a through-barrier optical-and-electrical connection between the OSS medical device and the relay module in accordance with some embodiments.

FIG. 6 illustrates a detailed view of the relay module 120 with a primary receptacle 632 for establishing optical or optical-and-electrical connections in accordance with some embodiments. FIG. 7 illustrates establishing a through-barrier optical or optical-and-electrical connection between the OSS medical device 110 and the relay module 120 in accordance with some embodiments. FIG. 9 illustrates the second medical system 200 in use during a patient procedure with the medical barrier 703 in accordance with some embodiments.

As shown, the relay module 120 includes the housing 324, the primary receptacle 632 disposed in the housing 324, one or more secondary receptacles such as secondary receptacle 634 disposed in the housing 324, one or more cables extending from the housing including a primary cable such as the cable 326 extending from the housing 324, and the optical fiber 628 extending through the housing 324 and along the cable 326. Again, the relay module 120 can include one or more electrical leads extending through the housing 324 and along the cable 326 or another cable (e.g., a secondary cable) of the one-or-more cables.

The primary receptacle 632 includes an optical receiver configured to accept insertion of an optical terminal of a plug of the OSS medical device 110 (e.g., the plug 322 of the PICC 310) for establishing an optical connection (e.g., a through-barrier optical connection) between the relay module 120 and the optical-fiber stylet of the OSS medical device 110 (e.g., the optical-fiber stylet 424 of the PICC 310) when the plug is inserted into the primary receptacle 632. The primary receptacle 632 can also include one or more electrical contacts configured to contact an electrical terminal of the plug of the OSS medical device 110 (e.g., a metal piece of the plug 322 of the PICC 310 corresponding to a barrier-piercing element 523 of the plug 322), when present, for establishing an electrical connection between the relay module 120 and the one-or-more electrical leads of the OSS medical device 110 simultaneously with the optical connection in an optical-and-electrical connection (e.g., a through-barrier optical-and-electrical connection) when the plug is inserted into the primary receptacle 632.

The one-or-more secondary receptacles (e.g., the secondary receptacle 634) are configured to accept insertion of a corresponding number of electrical plugs associated with the one-or-more electrical medical devices (e.g., the ECG patches 112, the arm band 114, etc.) and establish a corresponding number of electrical connections (e.g., under-barrier electrical connections) between the relay module 120 and the one-or-more electrical medical devices. For example, the relay module 120 of FIGS. 1 and 2 includes at least three secondary receptacles to accept insertion of three electrical plugs associated with the ECG patch 112a (e.g., a right-arm ECG patch), the ECG patch 112b (e.g., a left-leg ECG patch), and, optionally, the arm band 114 and establish three electrical connections (e.g., under-barrier electrical connections) between the relay module 120 and the foregoing electrical medical devices.

The one-or-more cables include one or more corresponding plugs for establishing one or more connections between the relay module 120 and a remainder of the medical system 100 or 200, which is configured to receive optical and electrical signals from the relay module 120. For example, the primary cable (e.g., the cable 326) of the one-or-more cables includes a primary plug (e.g., the plug 330) for establishing at least an optical connection (e.g., connection b or b" in FIG. 2) between the relay module 120 and the console 230 (i.e., the console 230 including the integrated optical interrogator 232) for shape sensing with the OSS medical device 110. Optionally, the primary plug is also for establishing an electrical connection (e.g., connection b" in FIG. 2) between the relay module 120 and the console 230 for at least generating ECG traces with the ECG stylet. Exclusive of the foregoing electrical connection (i.e., that of connection b" in FIG. 2), the one-or-more cables can include, for example, a secondary cable with a secondary plug for establishing one or more electrical connections (e.g., connection b' in FIG. 2) between the relay module 120 and the console 230 for generating ECG traces with the ECG patches 112, determining a reference frame with the arm band 114, or both. However, in some embodiments, only the primary cable and plug is needed for establishing all such optical and electrical connections. (See connection b" in FIG. 2.)

The optical fiber 628 extends from the primary receptacle 632 through the primary cable (e.g., the cable 326) to the primary plug (e.g., the plug 330). The optical fiber 628 is configured to convey the input optical signals from the optical interrogator 140 or 232 to the optical-fiber stylet of the OSS medical device 110 (e.g., the optical-fiber stylet 424 of the PICC 310) and the reflected optical signals from the optical-fiber stylet to the optical interrogator 140 or 232.

As set forth above, the relay module 120 can further include the one-or-more sensors 222 selected from the gyroscope, the accelerometer, and the magnetometer disposed within the housing 324. The one-or-more sensors 222 are configured to provide sensor data for determining a reference plane for shape sensing with the optical-fiber stylet of the OSS medical device 110 (e.g., the optical-fiber stylet 424 of the PICC 310).

The relay module 120 can further include an LED 636 disposed in the housing 324 proximate the primary receptacle 632. The LED 636 is configured to illuminate upon establishing an optical-and-electrical connection (e.g., connection b" in FIG. 2) or another electrical connection (e.g., connection b' in FIG. 2). When illuminated, the LED 636 is useful for finding the primary receptacle 632 when the relay module 120 is under the medical barrier 703.

The relay module 120 further includes one or more electrical leads extending from any number of receptacles including the primary receptacle 632 and the one-or-more secondary receptacles, the one-or-more sensors 222, if present, and the LED 636, if present, through any of the one-or-more cables (e.g., the cable 326) and corresponding plugs (e.g., the plug 330) thereof. In addition to any needed electrical power by the ECG stylet, the one-or-more electrical medical devices connected to the secondary receptacles, the one-or-more sensors 222, the LED 636, or the like, the one-or-more electrical leads are configured to convey input electrical signals from the console 130 or 230 to the ECG stylet, the one-or-more electrical medical devices connected to the secondary receptacles, the one-or-more sensors 222, the LED 636, or the like. The one-or-more electrical leads are also configured to convey any output electrical signals from the ECG stylet, the one-or-more electrical medical devices connected to the secondary receptacles, the one-or-more sensors 222, the LED 636, or the like to the console 130 or 230.

The relay module 120 is configured to sit beneath the medical barrier 703 on or alongside a patient P such as on a chest of the patient. As such, the relay module 120 need not require disinfection or sterilization. However, should the relay module 120 require disinfection or sterilization, the relay module 120 can be configured to be amenable to disinfection or sterilization. For example, the housing 324 of the relay module 120 can be non-porous or chemically resistant to oxidants. The relay module 120 can be configured for manual disinfection with a ChloraPrep® product by Becton, Dickinson and Company (Franklin Lakes, NJ), or the relay module 120 can be configured for automatic high-level disinfection or sterilization with vaporized $H_2O_2$ by way of Trophon® by Nanosonics Inc. (Indianapolis, IN).

While not shown, the housing 324 of the relay module 120 can include a loop extending from the housing 324, a tether point integrated into the housing 324, or a ball-lock-pin receiver integrated into the housing 324 configured for attaching a neck strap to the relay module 120. The loop, the tether point, or the ball-lock-pin receiver enables the relay module 120 to be secured to a neck of the patient P while sitting on the patient's chest. Additionally or alternatively, the housing 324 includes a patient-facing surface (e.g., a back of the relay module 120) configured to be adhered to the patient's chest. The patient-facing surface enables the relay module 120 to be secured to the patient while sitting on or alongside the patient whether or not the relay module 120 is also secured to the patient's neck.

Again, the primary receptacle 632 includes the optical receiver configured to accept insertion of the optical terminal of the plug of the OSS medical device 110 (e.g., the plug 322 of the PICC 310) and form an optical connection when the plug is inserted into the primary receptacle 632. The primary receptacle 632 can also include one or more electrical contacts configured to contact the electrical terminal (e.g., a metal piece of the plug 322 corresponding to the barrier-piercing element 523 of the plug 322) of the plug of the OSS medical device 110, when present, for establishing an electrical connection between the relay module 120 and the one-or-more electrical leads of the OSS medical device 110 when the plug is inserted into the primary receptacle 632. However, with the relay module 120, such optical and electrical connections are formed with the medical barrier 703 between the relay module 120 and the OSS medical device 110. The primary receptacle 632 and the plug of the OSS medical device 110 enable such connections from a sterile field (e.g., above the medical barrier 703 when a sterile drape) including the OSS medical device 110 such as the PICC 310 to a non-sterile field (e.g., beneath the medical barrier 703 when a sterile drape) including the relay module 120.

Other Embodiments

Figure 10:
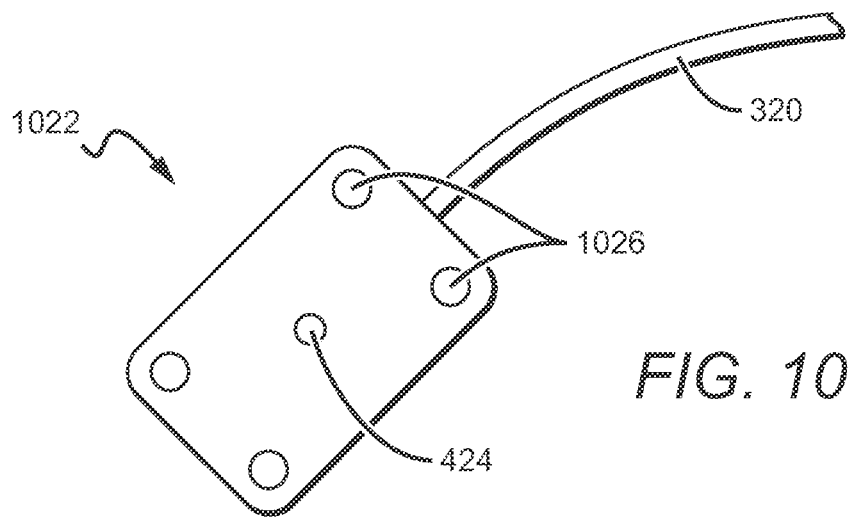
FIG. 10 illustrates an optical connector of the extension tube of the OSS medical device in accordance with some embodiments.
Figure 11:
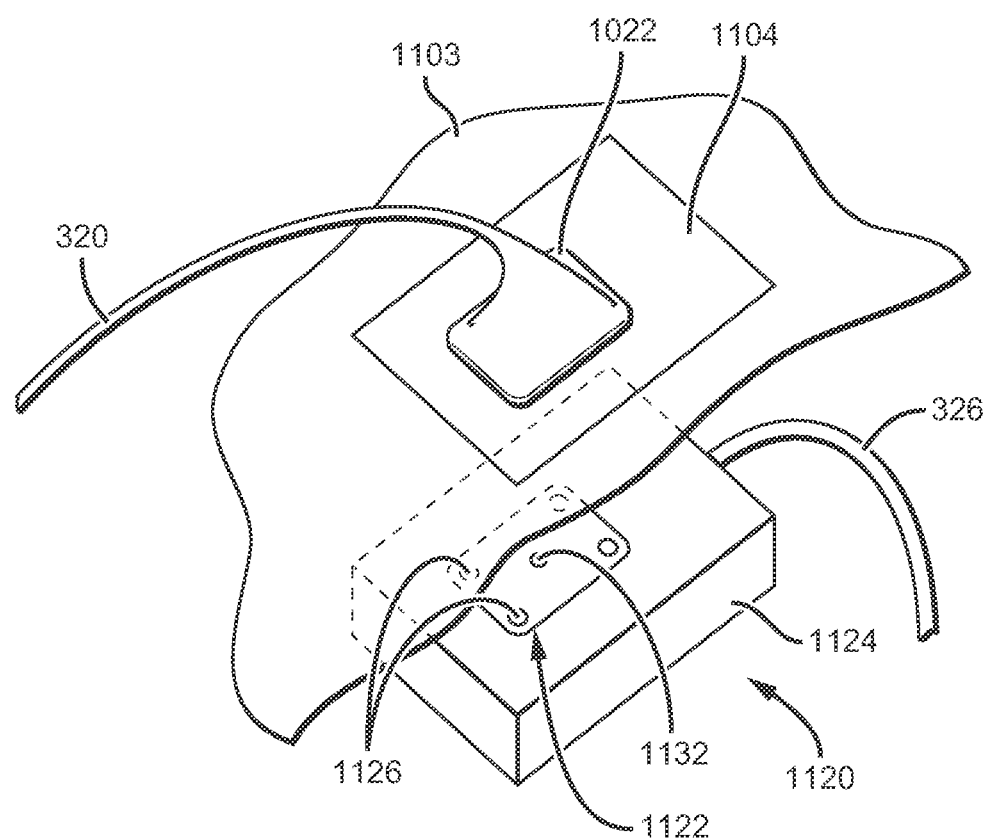
FIG. 11 illustrates an alternative relay module with an optical connector for establishing optical connections across a medical barrier in accordance with some embodiments.

FIG. 10 illustrates an optical connector 1022 of the extension tube 320 of the OSS medical device 110 in accordance with some embodiments. FIG. 11 illustrates an alternative relay module 1120 with an optical connector 1122 for establishing optical connections across a medical barrier 1103 in accordance with some embodiments.

As set forth above, the extension tube 320 can include one or more optical-fiber cores extending from the optical-fiber stylet 424 along a length of the extension tube 320. The one-or-more optical-fibers can extend to an optical terminal in a mating surface of the optical connector 1022.

The optical connector 1022 includes one or more alignment magnets 1026 disposed in the mating surface of the optical connector 1022 around the optical terminal or an end portion of the optical-fiber stylet 424.

As set forth above, the relay module 120 can be configured to relay optical signals to a receiver thereof such as the console 230 of the medical system 200. When the relay module 1120 is so configured, the relay module 1120 includes one or more optical-fiber cores within a housing 1124 of the relay module 1120 and the optical connector 1122. It should be understood the relay module 1120 can be further configured to relay electrical signals from the one-or-more electrical devices (e.g., the ECG patch 112*a*, the ECG patch 112*b*, the arm band 114, etc.) to the console 230 of the medical system 200 like the relay module 120.

The optical connector 1122 includes one or more alignment magnets 1126 disposed in a mating surface of the optical connector 1122 around an optical receiver 1132.

The optical connector 1022 and the optical connector 1122 are configured to mate across a transparent window 1104 of the medical barrier 1103 (e.g., a drape) and establish an optical connection between the optical terminal of the optical connector 1022 in a sterile field and the optical receiver of the optical connector 1122 in a non-sterile field.

A shape of each connector of the optical connector 1022 and the optical connector 1122 can be configured to enforce a particular orientation of the optical connector 1022 and the optical connector 1122 when mated across the transparent window 1104 of the medical barrier 1103. For example, each connector of the optical connector 1022 and the optical connector 1122 shown in FIG. 11 is rectangular or longer than it is wide, thereby enforcing two of the four most reasonable orientations for rectangular connectors.

Magnetic poles of the one-or-more alignment magnets 1026 and 1126 of each connector of the optical connector 1022 and the optical connector 1122 can additionally or alternatively be configured to enforce a particular orientation of the optical connector 1022 and the optical connector 1122 when mated across the transparent window 1104 of the medical barrier 1103. For example, a first side of the optical connector 1022 can include a first pair of the alignment magnets 1026 having a same magnetic pole orientation (e.g., N). A second side of the optical connector 1022 can include a second pair of the alignment magnets 1026 having a same magnetic pole orientation (e.g., S) but different than the first side of the extension-tube connector. The optical connector 1122 can be likewise configured such that similar sides of the optical connector 1022 and the optical connector 1122 repel each other when brought close to each other and dissimilar sides of the optical connector 1022 and the optical connector 1122 attract each other when brought close to each other. In this way, two of the four most reasonable orientations of, for example, square-shaped connectors can be enforced. However, if the optical connector 1022 and the optical connector 1122 are rectangular as shown in FIG. 11, both the shape and the magnetic poles configured as in the example can enforce a single orientation.

Notwithstanding the foregoing, a shape of each connector of the optical connector 1022 and the optical connector 1122 can be rotationally symmetric. Such a configuration allows a number of rotationally equivalent orientations of the optical connector 1022 and the optical connector 1122 when mated across the transparent window 1104 of the medical barrier 1103. For example, all the magnetic poles of the one-or-more alignment magnets 1026 of the optical connector 1022 can be of a same magnetic pole orientation but opposite all the magnetic poles of the one-or-more alignment magnets 1126 of the optical connector 1122 to complement all the magnetic poles of the one-or-more alignment magnets 1126 of the optical connector 1122. Indeed, such a configuration allows a number of rotationally equivalent orientations of the optical connector 1022 and the optical connector 1122 when mated across the transparent window 1104 of the medical barrier 1103.

Methods

FIG. 9 illustrates the second medical system 200 in use during a patient procedure with the medical barrier 703 in accordance with some embodiments.

A method of the medical system 100 or 200 can include a method of use during a medical procedure. For example, a method of using the medical system 200 during such a medical procedure includes a relay-module placing step, an electrical-plug inserting step, a medical-drape placing step, and a barrier-piercing-plug inserting step.

The relay-module placing step includes placing the relay module 120 on a surface (e.g., a relatively flat surface such as a chest of the patient P, a table beside the patient P, etc.), which establishes a reference plane for shape sensing with the OSS medical device 110. Prior to the relay-module placing step, the method can further include a disinfecting or sterilizing step of disinfecting or sterilizing the relay module 120 before placing the relay module 120 on or alongside the patient P.

The electrical-plug inserting step includes inserting one or more electrical plugs corresponding to one or more electrical medical devices into a corresponding number of secondary receptacles (e.g., the secondary receptacle 634) of the relay module 120. The electrical-plug inserting step establishes one or more under-barrier electrical connections—or soon-to-be one or more under-barrier electrical connections—between the one-or-more electrical devices and the relay module 120.

The medical-drape placing step includes placing the medical barrier 703 over the relay module 120, as well as any of the one-or-more electrical medical devices if already connected to the relay module 120. The medical-drape placing step establishes a sterile field over the relay module 120 and any of the one-or-more electrical devices connected thereto.

The barrier-piercing-plug inserting step includes inserting the barrier-piercing plug 322 of the OSS medical device (e.g., the PICC 310) through the medical barrier 703 and into the primary receptacle 632 of the relay module 120. The barrier-piercing-plug inserting step establishes a through-barrier optical connection or a through-barrier optical-and-electrical connection between the OSS medical device 110 in the sterile field and the relay module 120 in a non-sterile field.

The method further can further include an identifying step, a palpating step, or both. The identifying step includes identifying the LED 636 disposed in the housing 324 of the relay module 120 proximate the primary receptacle 632. The identifying step occurs after the establishing step set forth below, which illuminates the LED 636. The palpating step includes palpating the primary receptacle 632 under the medical barrier 703. Both the identifying step and the palpating step occur before the barrier-piercing-plug inserting step.

The method can further include an establishing step of establishing one or more connections between the relay module 120 and a remainder of the medical system 200 (e.g., the console 230) for relaying optical and electrical signals from the relay module 120. The one-or-more connections are selected from an optical connection, an optical-and-electrical connection, and an electrical connection. At least the optical-and-electrical connection (e.g., connection b" in FIG. 2) or the electrical connection as another electrical connection (e.g., connection b' in FIG. 2) between the relay module 120 and the console 230 are needed to provide power to the LED 636 for illumination thereof for the identifying step.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of a medical system, comprising:
    placing a relay module on a surface;
    inserting one or more electrical plugs corresponding to one or more electrical medical devices into a corresponding number of secondary receptacles of the relay module, thereby establishing one or more under-barrier electrical connections between the one or more electrical medical devices and the relay module;
    placing a medical barrier over the relay module, thereby establishing a sterile field above the medical barrier; and
    inserting a barrier-piercing plug of an optical shape-sensing ("OSS") medical device through the medical barrier and into a primary receptacle of the relay module, thereby establishing a through-barrier optical connection or a through-barrier optical-and-electrical connection between the OSS medical device in the sterile field and the relay module in a non-sterile field.

2. The method of claim 1, further comprising establishing one or more relay connections between the relay module and a remainder of the medical system for relaying optical and electrical signals from the relay module, the one or more relay connections selected from a relay optical connection, a relay optical-and-electrical connection, and a relay electrical connection, provided at least the relay optical connection or the relay optical-and-electrical connection is selected.

3. The method of claim 1, wherein the relay module includes one or more sensors selected from a gyroscope, an accelerometer, and a magnetometer disposed within a housing of the relay module, the one or more sensors configured to provide sensor data for determining a reference plane for shape sensing with the OSS medical device.

4. The method of claim 3, wherein placing the relay module on the surface includes placing the relay module on a table beside a patient, thereby establishing the reference plane for shape sensing with the OSS medical device.

5. The method of claim 3, wherein placing the relay module on the surface includes placing the relay module on a chest of a patient, thereby establishing the reference plane for shape sensing with the OSS medical device.

6. The method of claim 5, wherein placing the relay module on the chest of the patient includes adhering a patient-facing surface of the housing of the relay module to the patient, thereby securing the relay module to the patient.

7. The method of claim 1, wherein the relay module is amenable to high-level disinfection or sterilization.

8. The method of claim 7, further comprising disinfecting the relay module before placing the relay module on a chest of a patient as the surface, thereby enabling a reference plane to be established for shape sensing with the OSS medical device.

9. The method of claim 1, further comprising identifying an illuminated light-emitting diode ("LED") disposed in a housing of the relay module proximate the primary receptacle before inserting the barrier-piercing plug of the OSS medical device into the primary receptacle of the relay module.

10. The method of claim 9, wherein the LED disposed in the housing of the relay module is configured to illuminate upon establishing the one or more under-barrier electrical connections between the one or more electrical medical devices and the relay module for finding the primary receptacle of the relay module under the medical barrier.

11. The method of claim 1, further comprising palpating the primary receptacle under the medical barrier before inserting the barrier-piercing plug of the OSS medical device into the primary receptacle of the relay module.

* * * * *